US011737830B2

(12) United States Patent
Girardeau-Montaut et al.

(10) Patent No.: US 11,737,830 B2
(45) Date of Patent: Aug. 29, 2023

(54) SURGICAL NAVIGATION TRACKERS WITH GUARDS

(71) Applicant: DePuy Ireland Unlimited Company, Ringaskiddy (IE)

(72) Inventors: Daniel Girardeau-Montaut, Grenoble (FR); Nicolas Demanget, Saint-Egrève (FR); Anthony Leandri, Goncelin (FR)

(73) Assignee: DePuy Ireland Unlimited Company, Ringaskiddy (IE)

( * ) Notice: Subject to any disclaimer, the term of this patent is extended or adjusted under 35 U.S.C. 154(b) by 733 days.

(21) Appl. No.: 16/587,529

(22) Filed: Sep. 30, 2019

(65) Prior Publication Data
US 2020/0121400 A1    Apr. 23, 2020

(30) Foreign Application Priority Data
Oct. 23, 2018    (EP) .................................... 18306385

(51) Int. Cl.
*A61B 34/20*    (2016.01)
*A61B 34/00*    (2016.01)
(Continued)

(52) U.S. Cl.
CPC .............. *A61B 34/20* (2016.02); *A61B 34/37* (2016.02); *A61B 34/70* (2016.02); *A61B 46/10* (2016.02);
(Continued)

(58) Field of Classification Search
CPC combination set(s) only.
See application file for complete search history.

(56) References Cited

U.S. PATENT DOCUMENTS

2006/0140464 A1    6/2006    Feilkas et al.
2011/0286098 A1    11/2011    Haun et al.
(Continued)

FOREIGN PATENT DOCUMENTS

EP    1518508 A1    3/2005
EP    2998931 A2    3/2016
(Continued)

OTHER PUBLICATIONS

Extended European Search Report for Application No. 18306385.8, dated Apr. 12, 2019 (9 pages).
(Continued)

*Primary Examiner* — Scott Luan
(74) *Attorney, Agent, or Firm* — Condo Roccia Kopitw LLP

(57) ABSTRACT

Surgical navigation trackers with guards are described that can aid in protecting tracking elements from accumulating liquids thereon, which can negatively impact surgical navigation performance. The surgical navigation trackers described herein can be utilized with a variety of systems and procedures. For example, in one embodiment a system is described that includes a surgical device having an end effector configured for manipulating tissue and a surgical navigation tracker configured to be coupled to any of a surgical instrument and an anatomical structure. The surgical navigation tracker can include a tracking element and a guard configured to be positioned between the tracking element and the cutting tool, as well as a tracking unit configured to determine a position of the surgical navigation tracker.

22 Claims, 11 Drawing Sheets

(51) Int. Cl.
*A61B 34/37* (2016.01)
*A61B 46/10* (2016.01)
*A61B 90/00* (2016.01)

(52) U.S. Cl.
CPC .............. *A61B 2034/2055* (2016.02); *A61B 2090/3983* (2016.02)

(56) References Cited

U.S. PATENT DOCUMENTS

| | | |
|---|---|---|
| 2014/0318551 A1 | 10/2014 | Daly |
| 2015/0257838 A1 | 9/2015 | Huet et al. |
| 2016/0135816 A1 | 5/2016 | Lavallee et al. |
| 2016/0249988 A1 | 9/2016 | Pfeifer et al. |
| 2016/0270853 A1 | 9/2016 | Lavallee et al. |
| 2016/0274571 A1 | 9/2016 | Lavallee et al. |
| 2016/0279877 A1 | 9/2016 | Lavallee |
| 2018/0085133 A1 | 3/2018 | Lavallee et al. |
| 2018/0092699 A1 | 4/2018 | Finley |

FOREIGN PATENT DOCUMENTS

| | | | |
|---|---|---|---|
| EP | 3226801 A1 * | 10/2017 | ............. A61B 34/20 |
| EP | 3226801 A1 | 10/2017 | |
| EP | 3065651 B1 | 4/2018 | |
| WO | 2011/158113 A1 | 12/2011 | |
| WO | 2016/096984 A1 | 6/2016 | |
| WO | 2018/103945 A1 | 6/2018 | |
| WO | 2018/104439 A1 | 6/2018 | |
| WO | 2018/104523 A1 | 6/2018 | |
| WO | 2018/167246 A1 | 9/2018 | |

OTHER PUBLICATIONS

Roth, M et al., "A new less invasive approach to knee surgery using a vision-guided manipulator," Dec. 2000.

* cited by examiner

SURGICAL NAVIGATION TRACKERS WITH GUARDS

CROSS-REFERENCE TO RELATED APPLICATIONS

This application claims priority under 35 U.S.C. § 119 to European Application No. 18306385.8, filed Oct. 23, 2018, which is hereby incorporated by reference in its entirety.

FIELD

This disclosure relates generally to surgical instruments, systems, and methods, and more particularly to instruments, systems, and methods for tracking or navigating surgical instruments relative to portions of patient anatomy during a procedure. Such instruments, systems, and methods can be used in various procedures, including, e.g., robotic or robot-assisted orthopedic surgical procedures such as knee arthroplasty, spinal fusion surgery, etc.

BACKGROUND

Many different surgical procedures utilize some form of surgical navigation or tracking to aid in positioning surgical instruments relative to portions of patient anatomy during a procedure. One such type of procedure is robotic or robot-assisted surgical procedures, where surgical navigation can be important to correctly position a robotically controlled or assisted surgical instrument relative to a patient.

There are a number of known surgical navigation or tracking technologies, including a commonly utilized optical navigation or tracking system that utilizes, e.g., stereoscopic sensors to detect infra-red (IR) light reflected or emitted from one or more optical markers affixed to surgical instruments and/or portions of a patient's anatomy. By way of further example, a tracker having a unique constellation or geometric arrangement of reflective elements can be coupled to a surgical instrument and, once detected by stereoscopic sensors, the relative arrangement of the elements in the sensors' field of view, in combination with the known geometric arrangement of the elements, can allow the system to determine a three-dimensional position and orientation of the tracker and, as a result, the instrument or anatomy to which the tracker is coupled.

Such systems are not without drawbacks, however. One issue encountered with optical navigation or tracking systems is that system performance can be compromised when foreign matter or liquids, such as bodily fluids, are splashed or otherwise ejected onto the reflective elements. More particularly, the presence of foreign matter or liquid on the surface of a reflective element can interfere with the ability of, e.g., stereoscopic sensors to detect the reflective element. This can degrade the performance of the system in identifying various instruments or portions of anatomy being tracked, as well as accurately determining the position and orientation of such instruments or portions of anatomy once identified.

For example, many surgical procedures involve cutting bone or tissue using a powered cutting tool, such as a reciprocating saw blade, rotating burr, etc. These instruments can spray, splash, or otherwise eject small solids and liquids, such as blood, etc., during operation. If blood or other bodily fluids comes into contact with a reflective tracking element positioned near the surgical site (e.g., by virtue of being attached to an instrument in use during the procedure or a portion of anatomy being operated on) the above-described performance issues can result.

Accordingly, there is a need for improved surgical navigation or tracking systems that can prevent the accumulation of liquids, such as bodily fluids, or other foreign matter on trackers used to identify and position surgical instruments or portions of patient anatomy.

SUMMARY

In some embodiments, improved surgical navigation trackers are provided with guards to protect tracking elements from contact with foreign matter or liquid, e.g., bodily fluids, in a surgical field. The guards can in some embodiments be integrated into the surgical navigation tracker such that they are effective as soon as the tracker is coupled to a surgical instrument or portion of patient anatomy. The guards can have a variety of forms, including a single larger guard configured to shield an entire constellation or arrangement of tracking elements, as well as guards configured to shield individual tracking elements. In some embodiments, combinations of various types of guards can be included to provide multiple types of protection and/or protection from a plurality of angles or directions.

In one aspect, a surgical system is provided that can include a surgical device having an end effector configured to manipulate tissue and a surgical navigation tracker configured to be coupled to any of a surgical instrument and an anatomical structure. The surgical navigation tracker can include a tracking element and a guard configured to be positioned between the tracking element and the end effector. Still further, the system can include a tracking unit configured to determine a position of the surgical navigation tracker.

According to an embodiment, a surgical navigation tracker is provided that is configured to be coupled to any of a surgical instrument and an anatomical structure, the surgical navigation tracker including a plurality of tracking elements arranged in a fixed geometry relative to one another and a guard configured to be positioned between the tracking elements and an end effector of a surgical device configured to manipulate tissue so as to collectively shield at least two of the tracking elements from liquid or foreign matter from at least one direction. Advantageously, the tracker may further comprise a plurality of second guards, wherein each second guard is disposed adjacent to one of the plurality of tracking elements so as to individually shield its tracking element from liquid or foreign matter. By "collectively" is meant in the present text that the guard is shaped and positioned relative to the at least two tracking elements to be capable of protecting all of these tracking elements from liquid or foreign matter from the at least one direction. By contrast, "individually" means that each second guard is shaped and positioned relative to one respective tracking element to protect it from liquid or foreign matter. The guard and the second guards may cooperate to shield the tracking elements from different directions. The design of the guard and second guards may be based on a compromise between a large protection from liquid or foreign matter and a limited obstruction of the tracking elements. The guard, by providing a first shielding against liquid projections, may allow limiting the extent of the second guards and may thus reduce the risk of obstruction of the tracking elements by the second guards.

According to a particular embodiment, the tracker may comprise a frame having a post extending distally therefrom; wherein each tracking element is coupled to the frame along a proximal portion thereof, and the guard is coupled to the frame such that the guard is disposed distally of the tracking elements and the post extends distally beyond the guard.

The instruments and methods described herein can have a number of additional features and/or variations, all of which are within the scope of the present disclosure. In some embodiments, for example, the system can further include a second surgical navigation tracker configured to be coupled to any of a surgical instrument and an anatomical structure, the second surgical navigation tracker including a tracking element and a guard configured to be positioned between the tracking element and the end effector. While any of a variety of surgical navigation trackers can be employed, in certain embodiments each surgical navigation tracker can include a plurality of tracking elements arranged in a fixed geometry relative to one another.

As noted, in some embodiments the surgical navigation tracker can include a plurality of tracking elements arranged in a fixed geometry relative to one another. In some embodiments, the plurality of tracking elements can be reflective optical markers. Further, in certain embodiments, the reflective optical markers can be spherical in shape.

In certain embodiments, the system can further include a plurality of second guards, and each second guard can be disposed adjacent to one of the plurality of tracking elements. Each second guard can be configured to shield its adjacent tracking element from a first direction. In some embodiments, the guard of the surgical navigation tracker can be configured to shield the plurality of tracking elements from a second direction that is different from the first direction.

In some embodiments, each second guard can be configured to shield its adjacent tracking element from a plurality of directions. Further, the guard of the surgical navigation tracker can be configured to shield the plurality of tracking elements and, in some embodiments, can be configured to shield the plurality of tracking elements from a plurality of directions. In the case of either the guard or the second guard, shielding from a plurality of directions can be achieved using, e.g., a curved surface, an angled surface, a surface having a plurality of faces or portions arranged in different directions, etc.

The guards described herein can have a variety of forms. In some embodiments, for example, the guard of the surgical navigation tracker can be curved. In other embodiments, the surgical navigation tracker guard can be planar.

In some embodiments, the surgical navigation tracker can include a pin for coupling the tracker to an anatomical structure. In some such embodiments, the guard can be disposed between the pin and the tracking element.

In certain embodiments, the surgical navigation tracker can include a frame to which the tracking element and the guard are coupled.

In another aspect, a surgical navigation tracker is provided that can include a frame having a post extending distally therefrom, a tracking element coupled to the frame along a proximal portion thereof, and a guard coupled to the frame such that the guard is disposed distally of the tracking element and the post extends distally beyond the guard.

As with the aspects described above, a number of variations and additional features are possible. For example, in some embodiments the tracking element can include a plurality of tracking elements that are each coupled to the frame in a fixed geometry relative to one another. Further, in some embodiments the tracking element can be a reflective optical marker. Still further, in certain embodiments the tracking element can be spherical in shape.

In some embodiments, the tracker can further include a second guard coupled to the tracking element. The second guard can be disposed, in some embodiments, between the tracking element and the frame. In certain embodiments, the second guard can be curved, while in some embodiments the second guard can be planar. Additionally, in various embodiments the guard can be any of curved and planar as well. Further, in some embodiments the second guard can be configured to shield the tracking element from a first direction and the guard can be configured to shield the tracking element from a second direction that is different from the first direction. Still further, in some embodiments, any of the guard and the second guard can be configured to shield the tracking element from a plurality of directions.

In certain embodiments, the tracking element can include a plurality of tracking elements and the second guard can include a plurality of second guards each disposed adjacent to one of the plurality of tracking elements. Further, each second guard can be configured to shield its adjacent tracking element and the guard can be configured to shield the plurality of tracking elements.

In some embodiments, a distal end of the post can be coupled to a surgical pin. The surgical pin can be, for example, configured to be driven into bone to couple the tracker to a portion of a patient's anatomy.

In another aspect, a surgical method is provided that can include positioning a surgical robot relative to a patient's knee such that a cutting tool coupled to the robot can make one or more cuts to any of a distal end portion of the patient's femur and a proximal end portion of the patient's tibia. The method can further include coupling a first surgical navigation tracker to the patient's femur such that a guard of the first surgical navigation tracker is disposed between the cutting tool and one or more tracking elements of the first surgical navigation tracker. Still further, the method can include coupling a second surgical navigation tracker to the patient's tibia such that a guard of the second surgical navigation tracker is disposed between the cutting tool and one or more tracking elements of the first surgical navigation tracker.

While specific reference to a patient's knee is made above, in other embodiments a similar method can be carried out with respect to any of a variety of portions of patient anatomy, as described in more detail below. Other variations are possible as well. For example, in some embodiments coupling the first surgical navigation tracker to the patient's femur can include coupling the first surgical navigation tracker to one or more pins driven into the patient's femur and, after coupling the first surgical navigation tracker to the patient's femur, the guard can be disposed between the one or more pins and the one or more tracking elements of the first surgical navigation tracker. And in certain embodiments, coupling the second surgical navigation tracker to the patient's tibia can include coupling the second surgical navigation tracker to one or more pins driven into the patient's tibia and, after coupling the second surgical navigation tracker to the patient's tibia, the guard can be disposed between the one or more pins and the one or more tracking elements of the second surgical navigation tracker.

Any of the features or variations described above can be applied to any particular aspect or embodiment of the present disclosure in a number of different combinations. The absence of explicit recitation of any particular combination is due solely to the avoidance of repetition in this summary.

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure.

Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Further, in the present disclosure, like-numbered components of the embodiments generally have similar features. Still further, sizes and shapes of the devices, and the components thereof, can depend at least on the anatomy of the subject in which the devices will be used, the size and shape of components with which the devices will be used, and the methods and procedures in which the devices will be used.

FIGS. 1-6B illustrate embodiments of robotic surgical systems that can be utilized with the surgical navigation trackers described herein. While the illustrated embodiments and accompanying description make particular reference to knee surgery and, in particular, to total knee arthroplasty (TKA) wherein the anatomical structure to be cut is a joint formed of the femur and tibia, the devices, systems, and methods described herein are not limited to this application. Rather, the devices, systems, and methods described herein can be utilized in various applications involving robotic, robot-assisted, and non-robotic operations where one or more surgical instruments and/or portions of patient anatomy and/or other components are tracked using a surgical navigation or tracking system to determine their three-dimensional position and orientation in a surgical field. With regard to surgical procedures in particular, this can include, by way of example, any surgical procedure involving an osteotomy step, such as unicompartemntal knee arthroplasty (UKA), tibial or femoral osteotomy, patella resurfacing, hallux valgus surgery, hip surgery, shoulder surgery, spine surgery, ankle surgery, maxillofacial surgery, etc.

Figure 1:
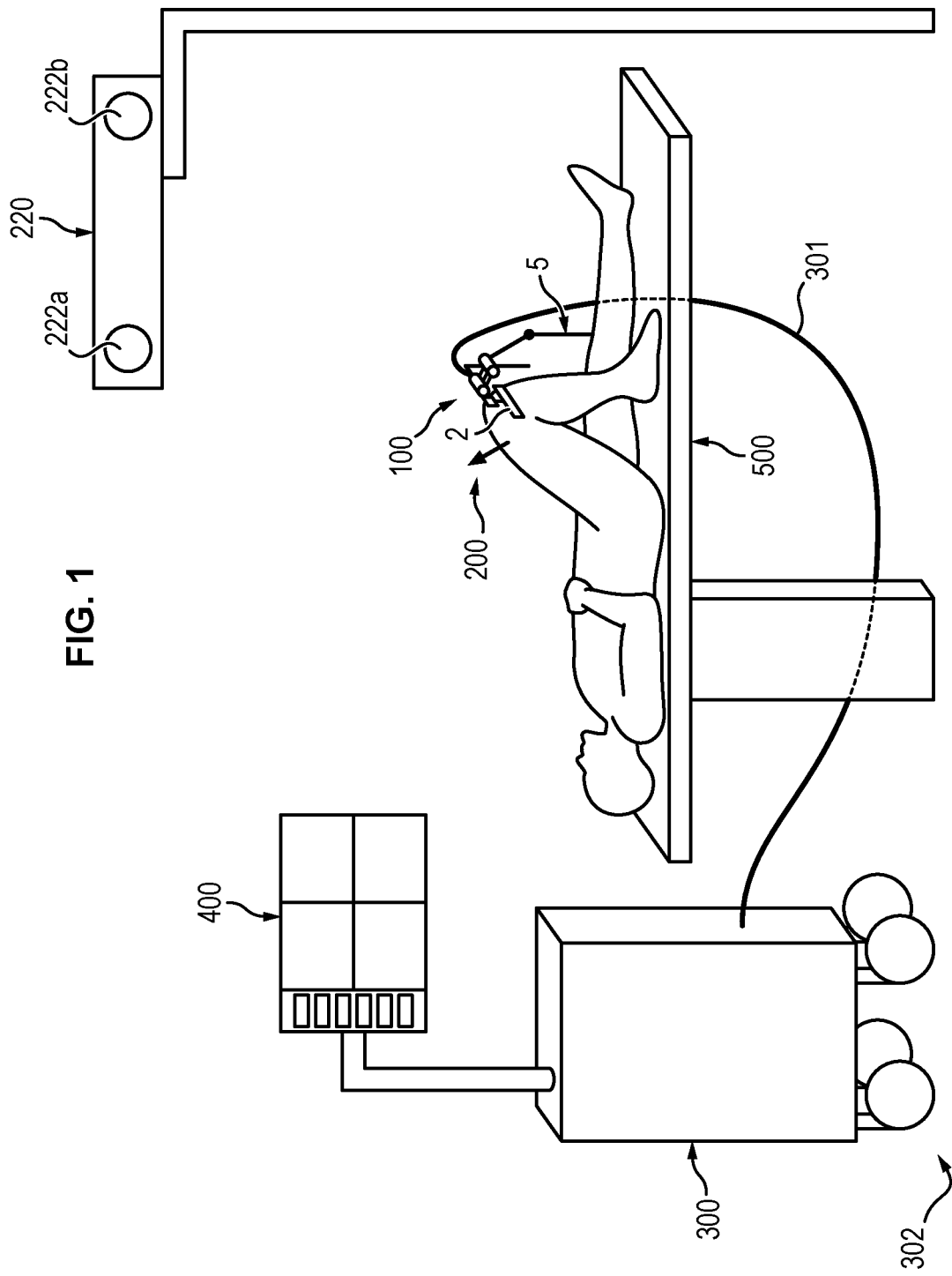
FIG. 1 is an illustration of a surgical system according to the present disclosure.

FIG. 1 shows an overview of one embodiment of a surgical system according to the present disclosure. Further details of surgical systems that can be utilized in connection with the present disclosure can be found in International Publication Nos. WO 2018/103945; WO 2018/104523; WO 2018/167246; WO 2018/104439; and U.S. Pat. Pub. No. 2016/0135816. The entirety of each of these publications is incorporated by reference herein. Returning to the figure, a patient P is shown lying on an operating table 500, e.g., about to undergo a total knee arthroplasty (TKA). A cutting tool, such as a saw 2, which is intended to cut the tibial and femoral bones along at least one target plane is used by a user, such as a surgeon. The cutting tool is held by the robotic device 100 and is constrained in each target plane by an actuation unit 4 (not shown in FIG. 1, but better seen in subsequent drawings). The robotic device 100 is connected to a control unit 300 that controls the actuation unit. Said control unit typically comprises power supply, AC/DC converters, motion controllers to power the motors of the actuation unit, fuses, real-time control system interface circuits, and other components conventionally included in surgical robot devices. As noted above, the description provided herein makes reference to the surgical system shown in FIG. 1 and the cutting tool 2, but the present disclosure is also contemplated for use with any surgical device having an end effector or tool configured to manipulate tissue. This could be a saw blade, mill, knife, or any other implement that could splash, spray, or otherwise eject liquid or foreign matter during use. Further, the present disclosure is also contemplated to include use of such instruments by surgical robots, by users with some degree of robotic assistance, and without involvement of surgical robots or robotic assistance.

Returning to the system illustrated in FIG. 1, the system also comprises a tracking unit 200, such that the relative pose or three-dimensional position and orientation of the device and the anatomical structure to be cut can be tracked in real time and shared between a real time control unit and a planning system. At least one coordinate system can be attached to the anatomical structure while at least one coordinate system can be attached to the cutting tool and/or the robotic device. The tracking unit can measure the relative motions between both coordinate systems in real time. Real time can, in some embodiments, mean high frequencies greater than twenty Hertz, in some embodiments in the range of one hundred to five hundred Hertz, with low latency, in some embodiments less than five milliseconds.

The tracking unit 200 can utilize any of a variety of trackers and tracking technologies known for use in surgical navigation. These can include, for example, optical trackers consisting of reflective or active markers detected by a sensor disposed inside or in view of the surgical field. In the illustrated embodiment, for example, the tracking unit 200 can include a passive optical tracker consisting of, for example, a constellation of reflective tracking elements (as shown in greater detail below) having a fixed geometric relationship that can be coupled to a portion of patient anatomy, a surgical instrument, or other component to be tracked. A stereoscopic sensor 220 having two or more physically separated detectors 222a, 222b can be used to detect light reflected off each of the tracking elements (e.g., reflected infra-red (IR) light in some embodiments). The sensor 220, in some embodiments in conjunction with other information processing components such as the control unit 300, can utilize the known fixed geometric relationship between the tracking elements and the detected positions of the tracking elements in the fields of view of the two detectors 222a, 222b to determine a precise three-dimensional position and orientation of the tracker (and therefore of the anatomy or instrument coupled thereto) within the surgical field.

In some embodiments, however, other types of surgical navigation and tracking can be employed in place of, or in addition to, the above-described reflective optical tracking. For example, in some embodiments optical tracking can be employed using active light emitters rather than reflective elements, such as light emitting diodes (LEDs). In other embodiments, electromagnetic trackers can be employed, while in still other embodiments any of inertial sensors using gyroscopic measurements, ultrasonic sensors, radio-frequency identification (RFID) sensors, or other known sensors can be employed.

Regardless of how it is gathered, position and orientation data can be transferred between components (e.g., to the control unit 300) via any suitable connection, e.g., with wires 301 or wirelessly using a low latency transfer protocol. The real-time control unit can carry out real-time control algorithms at a reasonably high frequency with low additional latency to coordinate movement of the robotic device 100.

Figure 2:
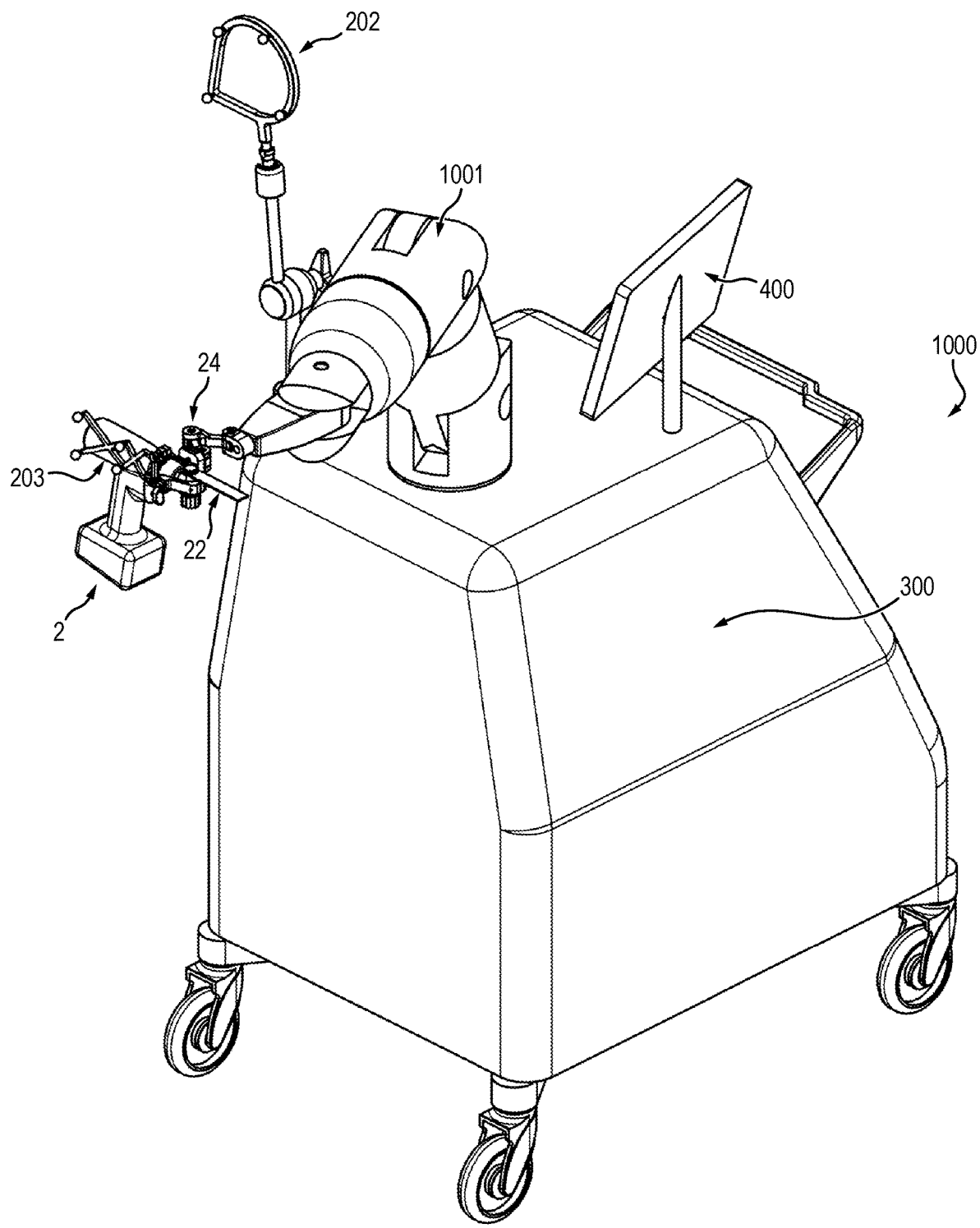
FIG. 2 is an illustration of one embodiment of a surgical robot according to the present disclosure.
Figure 3:
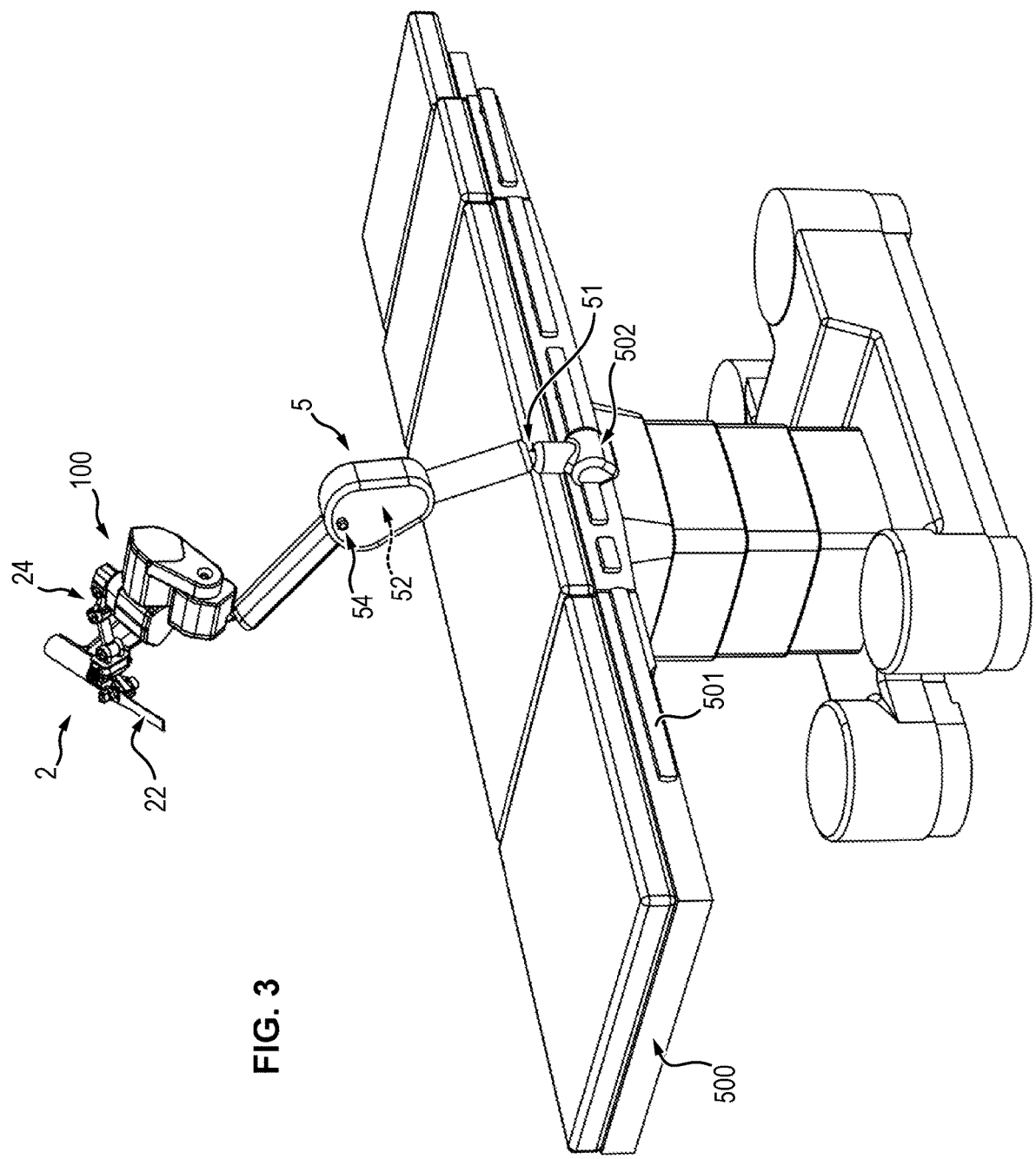
FIG. 3 is an illustration of another embodiment of a surgical robot according to the present disclosure.

FIGS. 2 and 3 illustrate different embodiments of a surgical system. In FIG. 2, for example, an integrated surgical robot 1000 can include the control unit and tracking unit in a cart 302 that can be moved in the operating room. The cart can include an articulating arm 1001 extending from the cart, as well as a holding mechanism 24 to interface the arm 1001 with the cutting tool 2. In some embodiments, however, various components, such as the control unit and tracking unit or components thereof, can be mounted on separate carts. In addition, articulated holding arms, lighting systems, or components of the tracking unit can be mounted directly on the anatomical structure or on some parts attached to the robotic device. For example, the cutting tool can rigidly support an electromagnetic emitter while electromagnetic sensors can be attached to the anatomical structure.

The system can also include a visual user interface 400 that is intended to display feedback information to a user and enable system configuration by the user. The feedback information can include indications regarding cutting planes, patient or instrument positioning, directions to achieved desired positioning, etc. The user interface 400 can include a screen, which can be located on a cart in the operating room, e.g., on the same cart 302 as the control unit and tracking unit, or on a separate cart, or attached to the walls or the ceiling of the operating room. Moreover, in addition to or instead of a screen, the user interface can include one or more indicators arranged on the robotic device itself to provide information to the user. For example, the indicator(s) can be made of LEDs arranged to indicate arrows, numbers or letters, or a miniature display.

FIG. 3 illustrates an embodiment of a surgical system wherein the robotic device 100 is coupled to a holding arm 5 that is fixed to a rail 501 of an operating table 500 by a clamp 502. In embodiments such as those illustrated in FIG. 3, the robotic device 100 can be coupled (e.g., using wires or wireless connections, etc.) to one or more carts including above-described components, such as the control unit 300, interface 400, etc. The robotic device 100 can include a cutting tool 2 coupled to an actuation unit 4 using a holding mechanism 24, as described herein. The robotic device 100 can in turn be coupled to the holding arm 5. The holding arm 5 shown in FIG. 3 can be made of several articulated segments using ball-and-socket joints, rotational and/or translational joints. In the illustrated example, the holding arm can be formed of the following kinematic links, in a sequence starting from the clamp: a pivot link 51 and a ball joint 52. A central module 53 can be provided with an actuator 54 that can allow unlocking of the holding arm when pushed. Alternatively, such an actuator could be arranged on a higher part of the holding arm so as to manipulate the arm and the robotic device 100 easily in case the user wants to change the position of the robotic device relative to the anatomical structure.

The holding arm 5 can be lockable, either manually by a knob (mechanical locking system) or actively by a dedicated actuator of a locking system. The locking system can be an electrical system, a piezoelectric system, a hydraulic system, a pneumatic system or a combination of such systems (e.g., a hydraulic cylinder driven by an electric motor). The actuator can be a button, a foot switch, a remote button, etc. To manipulate the robotic device 100, the user can maintain the actuator in an activated state until the desired positioning of the robotic device has been achieved.

The robotic device 100 shown in FIG. 3 can also include an actuation unit 4. The actuation unit 4 can have a serial architecture made of a plurality of mobile segments. In some embodiments, the actuation unit can have three motorized rotational degrees of freedom for adjusting the position and orientation of a cutting tool relative to target anatomy. In other embodiments, the actuation unit can have two motorized rotational degrees of freedom and one or two motorized translational degrees of freedom. Generally speaking, the actuation unit can include one or more, and in some embodiments from three to five, motorized degrees of freedom. In some embodiments, at least two of the motorized degrees of freedom can be rotational degrees of freedom orthogonal to each other. In some embodiments, the actuation unit can include three rotational motorized degrees of freedom.

The segments and their components can be integrated in an optimal way such that the robotic device 100 remains as compact and light as possible while remaining strong enough to be able to hold the cutting tool, as well as resist normal pressure applied by the user when he/she manipulates the cutting tool. In some embodiments, the segments of the actuation unit 4 can be arranged such that the rotation axes of two adjacent segments are substantially parallel to each other while axes of segments separated by an intervening segment can be substantially orthogonal to one another. Such an arrangement can provide an advantage in certain procedures, such as a total knee arthroplasty (TKA), where both the tibial cut and the femoral cuts can be made with a single initial position of the robotic device 100.

As shown in FIGS. 2 and 3, in some embodiments the cutting tool can be a surgical saw 2 coupled to the actuation unit 4. The saw 2 can include a saw blade 22 that oscillates in a determined plane (which can be referred to as the "cutting plane"). Thus, the saw blade can be operated to cut an anatomical structure according to a target plane without requiring any cutting block, provided that the actuation unit 4 constrains the saw in the target plane in real time. Usually, the cutting plane is parallel to the longitudinal axis of the saw 2 and the saw blade 22 oscillates on both sides of this axis—such a saw is sometimes known as a "sagittal saw." According to an embodiment, the saw blade can move back and forth along the longitudinal axis of the saw or a housing thereof—such a saw is sometimes known as a "reciprocating saw."

In certain embodiments, other cutting tools can be utilized. For example, according to another embodiment, the cutting tool can be a rotary burr. In some cases, if the burr head is small (e.g., with a diameter of the order of a few millimeters or less), the operation of the burr constrained in a cutting plane can allow for the creation of a planar cut. The burr tip can be spherical or cylindrical in various embodiments. According to still another embodiment, the cutting tool can be a laser with a system to control the depth of penetration of the laser to avoid damaging soft tissues behind the desired target region (e.g., a bone, etc.). According to yet another embodiment, the cutting tool can be a high-pressure water jet or any other device that creates cuts in an anatomical structure. Moreover, in still other embodiments, e.g., those for cutting soft tissues, the cutting tool can be a scalpel or any electrically activated device such as a lancet.

Figure 4:
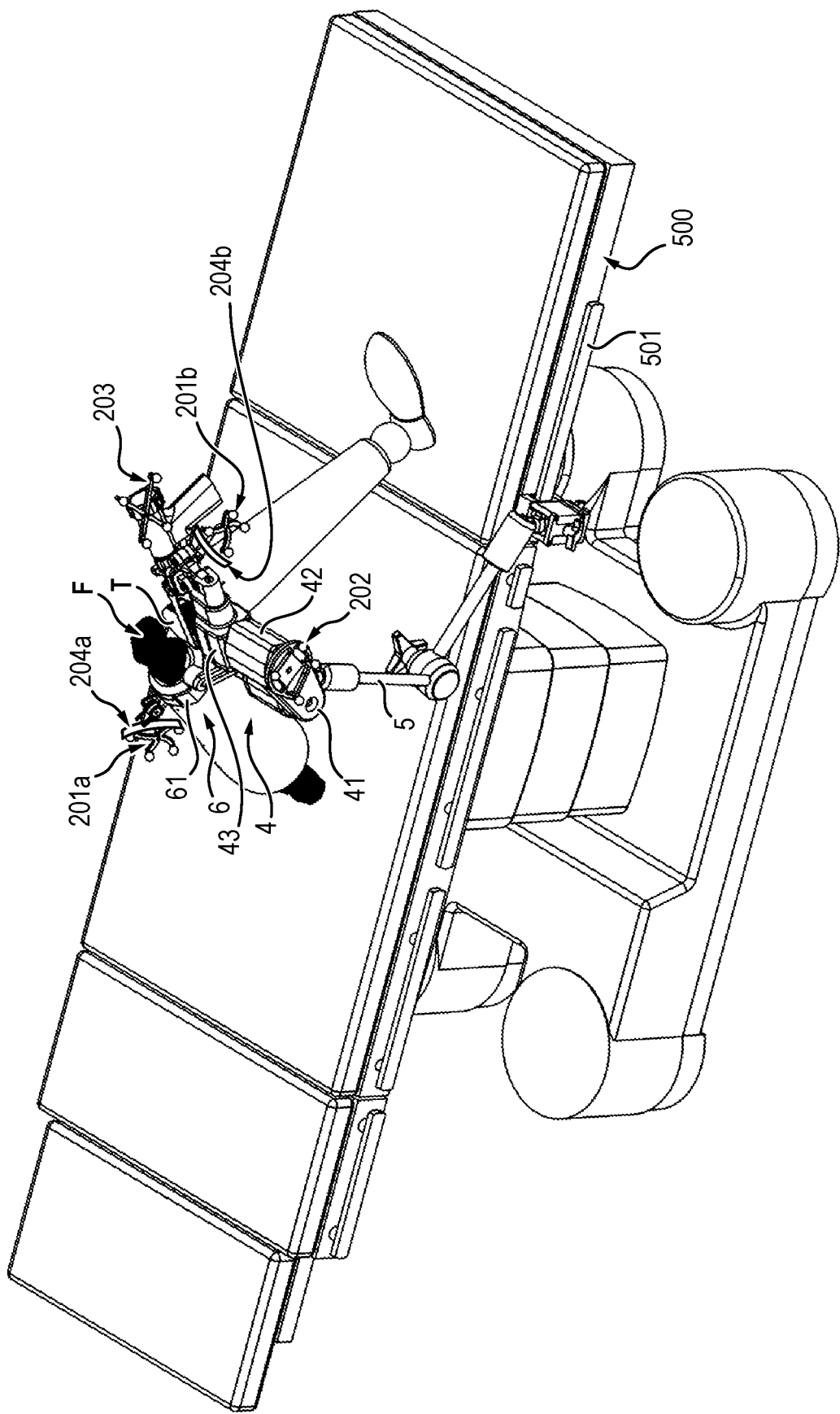
FIG. 4 is an illustration of one embodiment of a setup of the surgical robot of FIG. 3.
Figure 5:
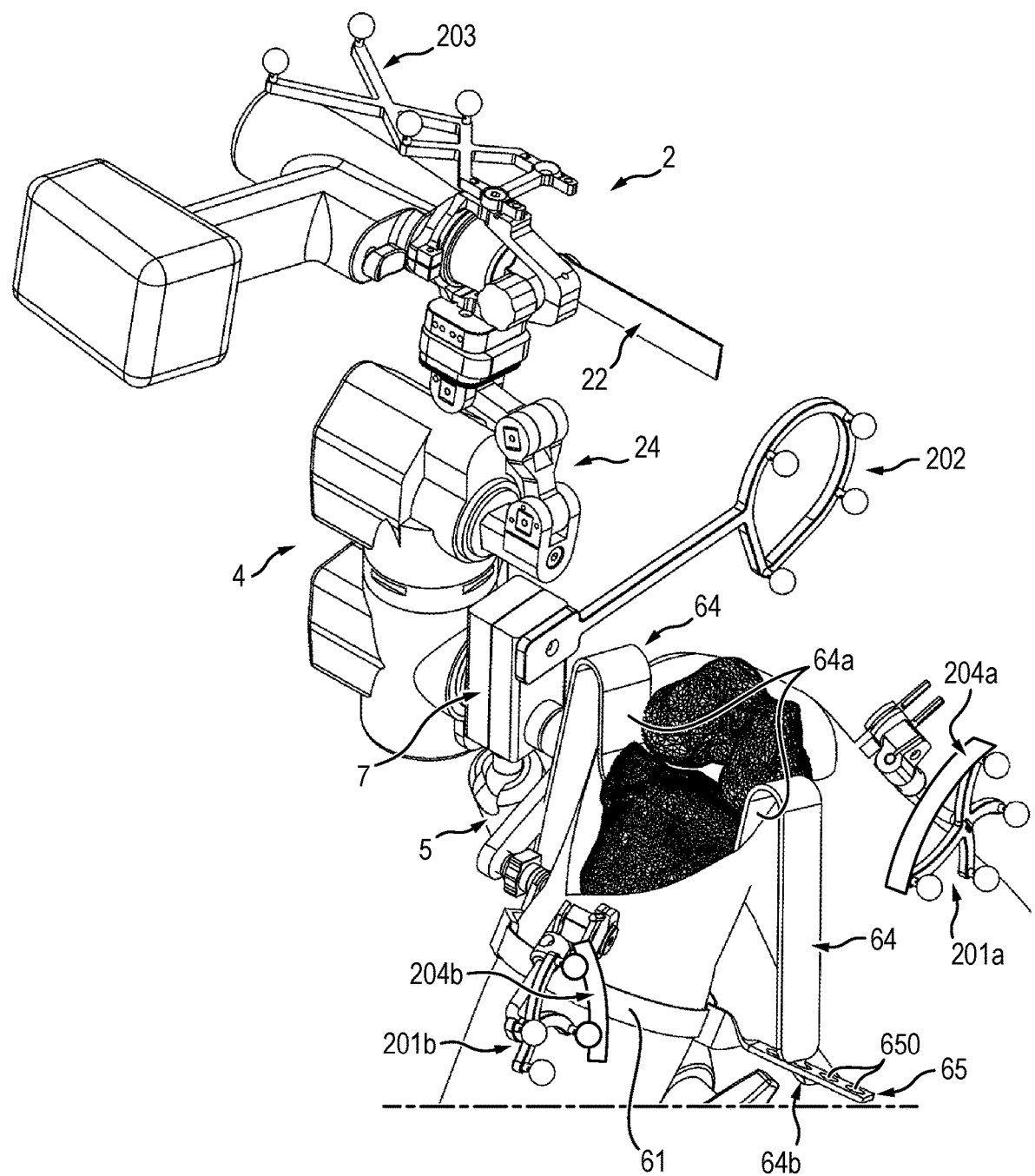
FIG. 5 is a detail view of the setup of the surgical robot of FIG. 4.
Figure 6A:
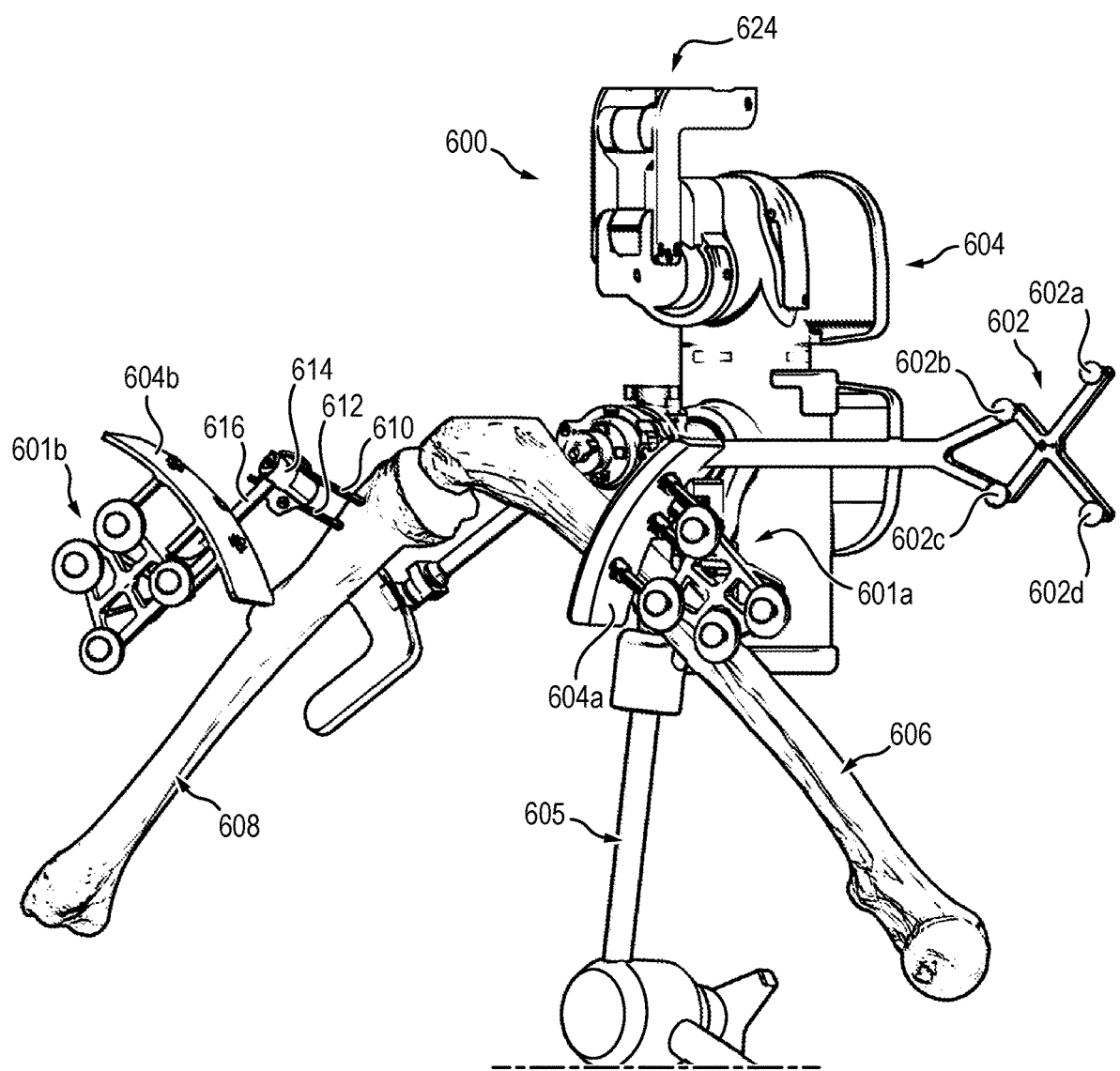
FIG. 6A is a perspective view of another embodiment of a surgical robot according to the present disclosure.
Figure 6B:
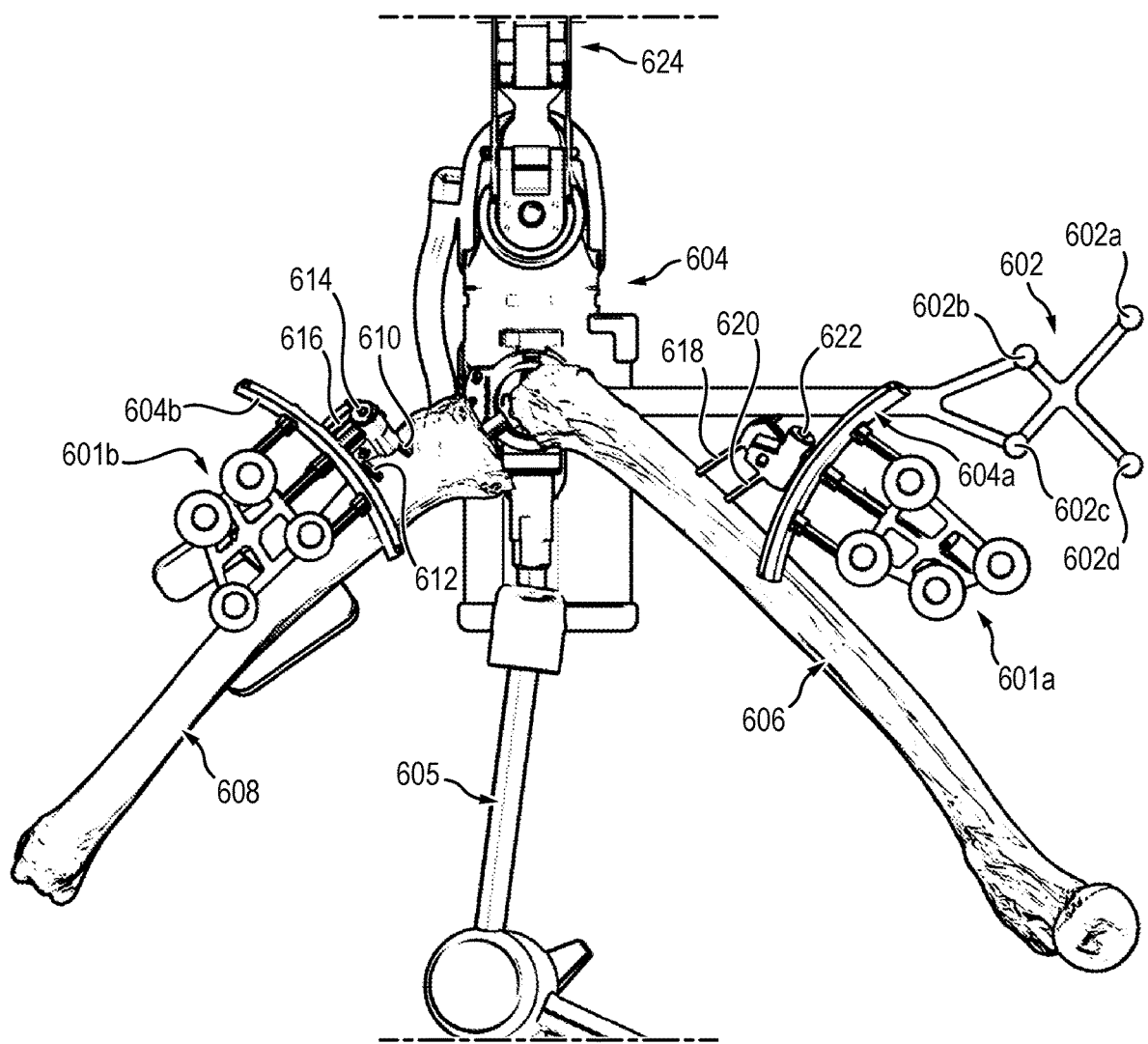
FIG. 6B is a front view of the surgical robot of FIG. 6A.

FIGS. 4 and 5 illustrate one embodiment of a setup of the robotic device illustrated in FIG. 3. A patient (only one leg is represented in FIGS. 4 and 5) is lying on an operating table 500, with the leg in flexed position. Although not illustrated, the patient's leg can be maintained in a flexed position by wedges commonly used in surgical interventions. For example, one wedge can be placed under the foot and another one can be placed on the external side of the hip, in order to reduce inward and outward movements of the flexed leg.

The holding arm 5 can have one end attached to a rail 501 arranged on the operating table 500 and the opposite end attached to the actuation unit 4 of a robotic device 100. The rail to which the holding arm is attached can be the rail located on the same side of the table as the leg of interest, or the rail located on the side of the table opposite to the leg of interest.

The actuation unit can also be attached to a strap 61 arranged around the upper leg, which can provide a support unit 6 creating a partial mechanical link between an anatomical structure (e.g., the patient's leg) and the actuation unit 4. Due to the fact that the support unit can make either direct contact with the anatomical structure to be cut or indirect contact via a region of the patient's body adjacent to the anatomical structure to be cut (here, the soft tissues surrounding the femur), the support unit can have the effect of a partial mechanical link that limits the movements of the user when operating the device—and, in some embodiments, also damps movements of the user and/or the patient, vibrations of the cutting tool, and reaction forces caused by movements of the actuation unit. The support unit 6 can be attached to an intermediate part 7 that is itself removably attached to the holding arm 5. In particular, the intermediate part 7 can allow making a sterile connection with the holding arm 5 over a sterile drape (not shown). The intermediate part 7 can carry a surgical navigation tracker 202 in some embodiments.

As shown in FIG. 5, one or more retractors 64 can also be positioned to assist in accessing a surgical site. The retractors 64 can pull the soft tissues to offer a large incision and vision to the surgeon. In some embodiments, a first retractor can be attached to the medial side of the incision and to the back part of the support unit 6 using a link that can be tensioned. A second retractor can be attached to the lateral side of the incision and to the back part of the support unit 6 using a link that can be tensioned. During maneuvers of the leg, the support unit 6 can be detached from the actuation unit 4 or holding arm 5 or intermediate part 7 using a fast but strong mechanical connection.

Each retractor 64 can have a bent shape, with a first end 64a configured to make contact with the anatomical structure and a second end 64b configured to be attached to the strap 61 of the support unit. More precisely, two bars 65 can include a slot through which the strap 61 passes, so that the bars 65 are maintained in a direction projecting away from the leg. Each bar can include a plurality of holes 650. The second end 64b of each retractor can be inserted into a selected hole 650 of the respective bar 65 such that the first end 64a of the retractor bears against the anatomical structure and sufficiently pulls the soft tissues.

Also shown in FIGS. 4 and 5 are various trackers that can be affixed to the components of the surgical system. For example, a first tracker 201a can be fixed to the femur and another tracker 201b can be fixed to the tibia. A tracker 202 can also be fixed to the actuation unit 4 of the robotic device. And a tracker 203 can be attached to the saw 2 that is coupled to the actuation unit 4, which allows compensating for any mechanical play that may exist between the saw and the remainder of the robotic device. In some embodiments, however, no tracker need be attached to the cutting tool. In this way, the cutting tool need not bear the weight of the tracker and the region of operation of the cutting tool can be freed from the tracker.

Tracking systems commonly used in computer-assisted surgery can use a variety of different technologies (e.g., passive optical, active optical, electromagnetic, inertia with gyroscopic measurements, ultrasonic, etc.) that can be used individually or in combination. According to some embodiments, the tracking system can be based on passive optical technology. Data gathered by tracking positions and orientations of the trackers can be combined with other data. For example, the positions of each moving segment of the actuation unit can be known in real time thanks to encoders or sensors of the motors controlling the various degrees of freedom provided by the actuation unit, and a calibrated model of the robot that includes all axes and distances of the robot segments. Using this model, and well-known geometric modeling techniques in robotics, it can be possible to calculate the relative positions of all segments, so if one measurement is known in a coordinate system attached to the robotic device using a surgical navigation tracker, then any segment position can also be known in the same coordinate system. Additionally, if a tracker is attached to the base of the actuation unit 4 and a second tracker is attached to an anatomical structure (e.g., the patient's leg), then the position and orientation of any segment of the actuation unit 4 can be known in the coordinate system attached to the tracker of the anatomical structure.

One issue encountered in surgical procedures employing passive optical surgical navigation or tracking systems is impaired tracking performance due to tracking elements being splashed with, or otherwise accumulating, foreign material such as bodily fluids, etc. on an outer surface thereof. For example, during operation of the saw 2 or other cutting tool, blood or other bodily fluids or foreign matter can be sprayed onto components near the cut site, which can include the trackers 201a, 201b, etc. Passive optical tracking systems utilize individual tracking elements having an outer reflective surface, e.g., a spherical outer reflective surface that can be easily detected using, e.g., the stereoscopic detector 220 described above. If blood or other foreign matter covers a portion or more of one or more of the tracking elements of one or more trackers, it can negatively impact performance of the tracking unit or system in detecting a particular tracker and determining a three-dimensional position and orientation thereof. Besides, when the tracking elements are standard reflective paper spheres, they can be hardly cleaned and thus need to be replaced during the surgical intervention, which increases the operating time.

Accordingly, and as shown in FIGS. 4-8B, trackers according to the present disclosure can include guards 204a, 204b disposed between the individual tracking elements and the surgical site and/or cutting tool 2 to shield at least part of the tracking elements from liquid spray or other foreign matter that may be ejected from the surgical site and/or cutting tool 2 during the procedure. Because the surgical field is usually viewed from a remote perspective, or multiple remote perspectives, by tracking unit detectors (e.g., sensor 220 described above), the presence of the guards 204a, 204b does not interfere with detection of the tracking elements by the tracking unit detectors (or the positioning of the trackers can be adjusted to eliminate any issue while maintaining the effectiveness of the guards). After positioning, the guards can effectively shield the tracking elements from foreign matter or liquid that may be ejected from the surgical site.

FIGS. 4 and 5 schematically illustrate the above-described guards 204a, 204b coupled to the trackers 201a, 201b that are coupled to a patient's femur and tibia, respectively, in the above-described knee arthroplasty operation. Note that guards can also be included in some embodiments on the other surgical navigation trackers included in the illustrated system, e.g., the tracker 202 coupled to the intermediate part 7 and actuation unit 4, and the tracker 203 coupled to the saw 2.

FIGS. 6A-8B provide alternative views of surgical navigation trackers including guards. For example, the alternative views of a surgical system shown in FIGS. 6A and 6B include a robotic device 600 as described above, e.g., including an actuation unit 604 coupled to a holding arm 605 to position the unit near a surgical site, e.g., the knee joint between a patient's femur 606 and tibia 608 in the illustrated embodiment (though, as described above, the present disclosure can be applied to surgical procedures performed at a variety of sites across the body). The actuation unit 4 can be coupled to a cutting tool (not shown) or other surgical instrument via a holding mechanism 624 such that the cutting tool or other surgical instrument can be positioned relative to the knee joint or other surgical site to perform cutting or other surgical operations. Further, one or more surgical navigation trackers, such as tracker 602, can be coupled to a portion of the actuation unit 604 or other portion of the robotic device to allow a surgical navigation or tracking system to determine the three-dimensional position and orientation of any component of the robotic device, as described above.

In the illustrated embodiment, the tracker 602 includes a constellation of a plurality of passive optical tracking elements 602a, 602b, 602c, 602d arranged in a fixed geometry relative to one another. The tracking elements 602a, 602b, 602c, 602d can be, for example, reflective spherical elements that can be detected by, e.g., a stereoscopic sensor 220, as described above. The sensor 220 can detect the unique fixed geometry of the tracking elements 602a, 602b, 602c, 602d to both identify the tracker 602 among other trackers in the surgical field and determine a three-dimensional position and orientation of the tracker 602 in the surgical field. While the description below regarding tracker 602 and other trackers focuses on reflective spherical tracking elements utilized in a passive optical surgical navigation or tracking system, other types of tracking systems and tracking elements can also be employed, as described above. For example, in some embodiments one or more active optical tracking elements might be employed in place of a constellation of passive optical tracking elements, etc.

In addition to the tracker 602 coupled to the robotic device 600, the system includes one or more trackers coupled to anatomic structures to be operated on by the robotic device. In the illustrated example of a total knee arthroplasty (TKA), this can include a first surgical navigation tracker 601a coupled to a patient's femur 606 and a second surgical navigation tracker 601b coupled to a patient's tibia 608. The surgical navigation trackers 601a, 601b can each include one or more tracking elements that can be detected by a tracking unit or system to determine a position of the tracker. In the illustrated embodiment, each tracker 601a, 601b can include a constellation of tracking elements arranged in a fixed geometry, as described in further detail below and similar to the above-described tracker 602 coupled to the robotic device 600. In other embodiments, however, one or more other types of tracking elements can be employed instead.

Each of the surgical navigation trackers 601a, 601b can also include a guard 604a, 604b coupled thereto and arranged so as to shield the one or more tracking elements from foreign liquids or matter that might be ejected from the surgical site during a procedure. Accordingly, the guards 604a, 604b can be positioned such that they are disposed between the one or more tracking elements of the trackers 601a, 601b and the cutting tool or other surgical instrument coupled to the robotic device 600 via, e.g., the holding mechanism 624.

Each surgical navigation tracker 601a, 601b can be coupled to an anatomic structure using any of a variety of securement mechanisms. For example, the surgical navigation tracker 601a can be coupled to the femur 606 using one or more surgical pins 618, 620 and the surgical navigation tracker 601b can be coupled to the tibia 608 using one or more surgical pins 610, 612. The surgical pins can be driven into the patient's bone prior to attachment of a surgical navigation tracker in some embodiments. For example, a surgeon or other user can drive pins 610, 612 into the tibia 608 and couple thereto an attachment mechanism 614. The attachment mechanism 614 can be configured to receive the surgical pins 610, 612, as well as a post 616 that is part of the surgical navigation tracker 601b. The mechanism 614 can provide one or more degrees of freedom to manipulate a position of the tracker 601b relative to the tibia 606 to achieve a position that is visible to the tracking system sensor(s), not obstructing access to the surgical site, and positioned such that the guard 604b can effectively shield the tracking element(s) from foreign liquid or matter splashed or otherwise ejected from the surgical site. The mechanism 614 can then be tightened to hold the tracker 601b in a fixed position relative to the tibia 608. The tracker 601b can thereafter be registered and utilized by a tracking system to determine a position of the tibia. A similar attachment mechanism 622 shown in FIG. 6B can be utilized to couple the tracker 601a to the femur 606. While surgical pins are described above, in other embodiments alternative mechanisms for attaching and holding a surgical navigation tracker relative to an anatomic structure can be utilized. For example, in certain embodiments suitably tensioned straps or other attachment mechanisms can be utilized so long as they can provide a rigid and stable connection between the tracker and anatomic structure such that a position of the tracker can be utilized to determine a position of the anatomic structure.

Figure 7A:
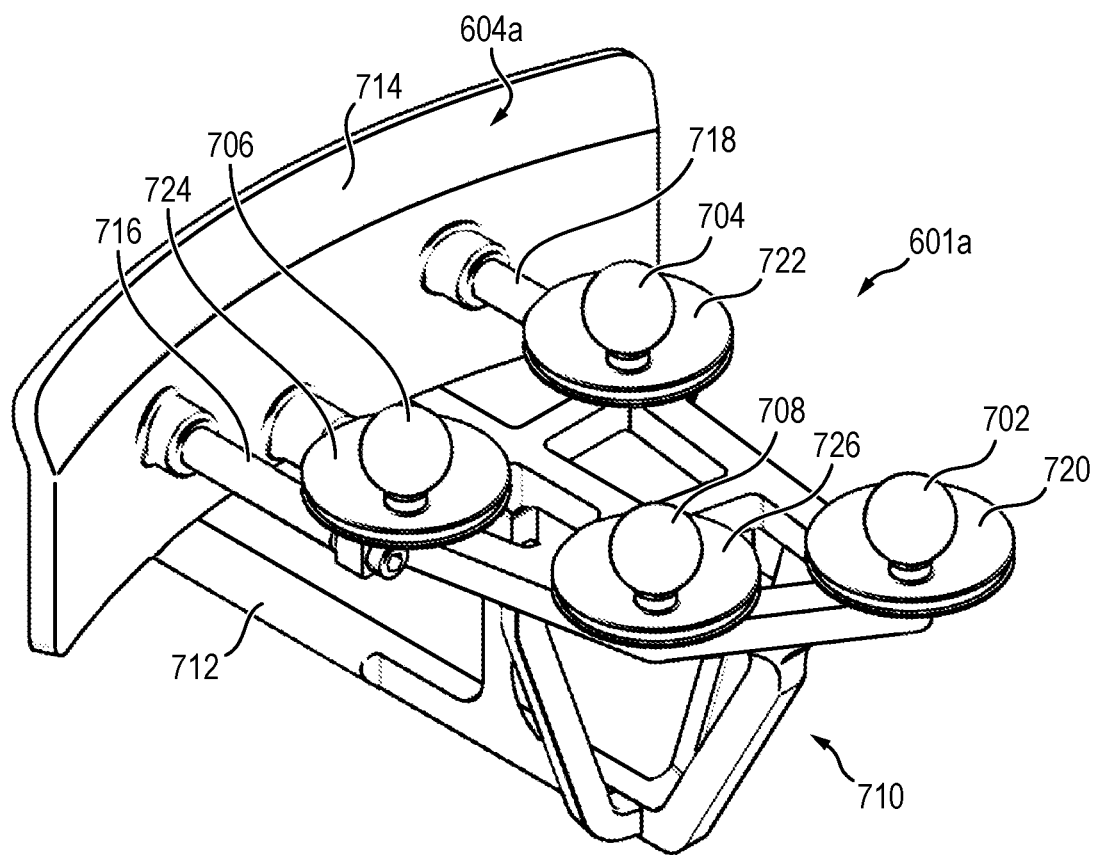
FIG. 7A is a perspective view of one embodiment of a first surgical navigation tracker according to the present disclosure.
Figure 7B:
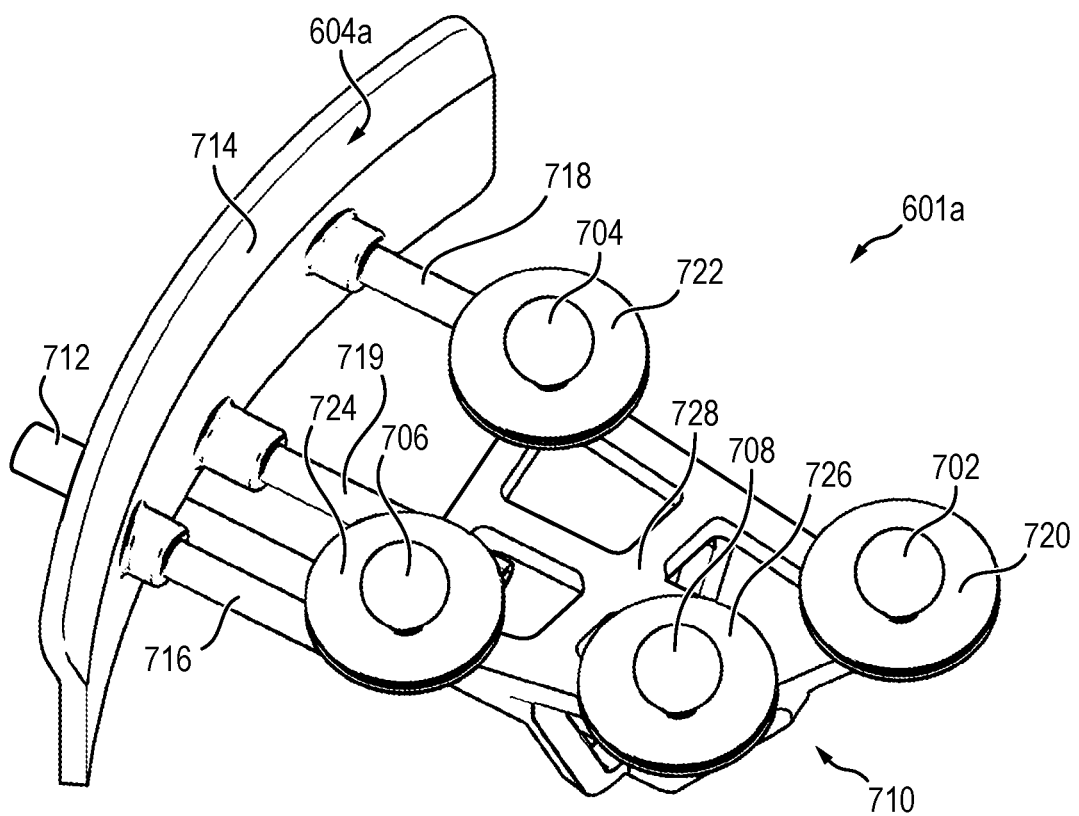
FIG. 7B is an alternative perspective view of the first surgical navigation tracker of FIG. 7A.
Figure 8A:
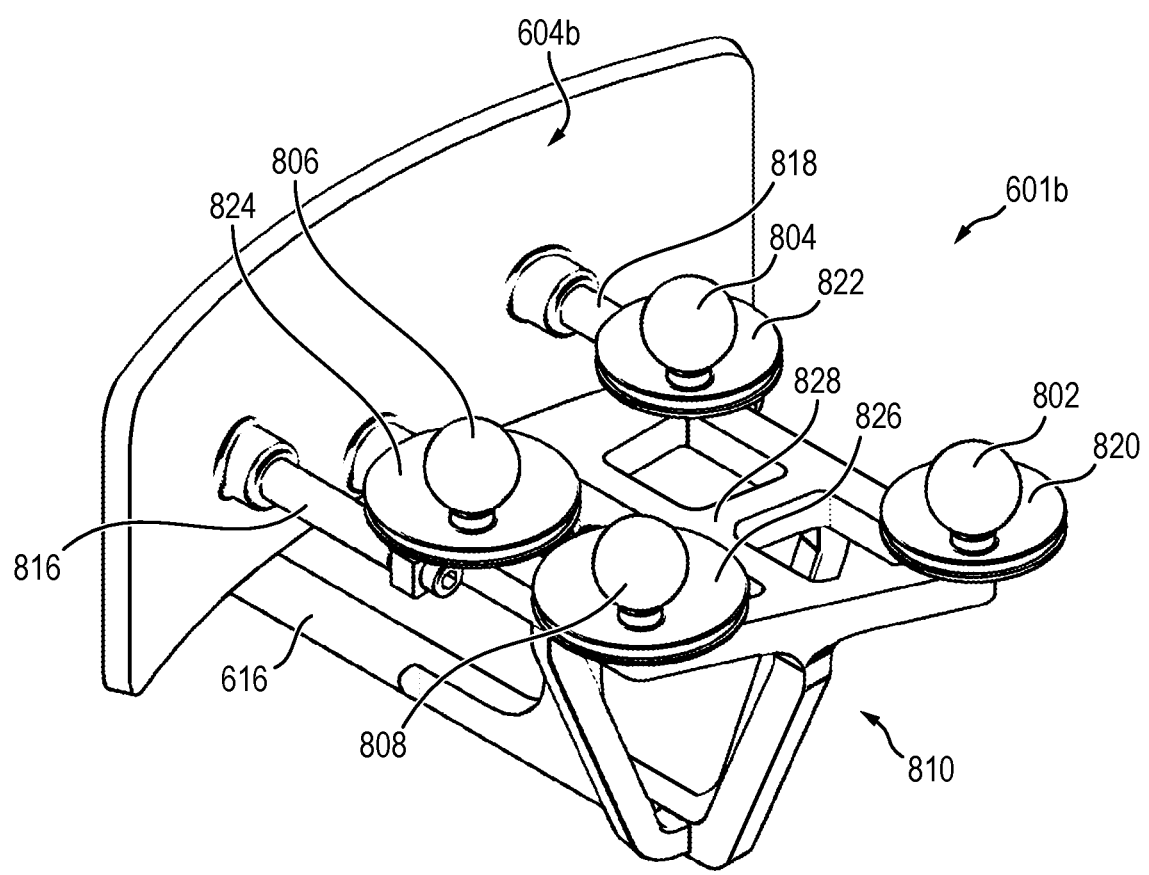
FIG. 8A is a perspective view of one embodiment of a second surgical navigation tracker according to the present disclosure.
Figure 8B:
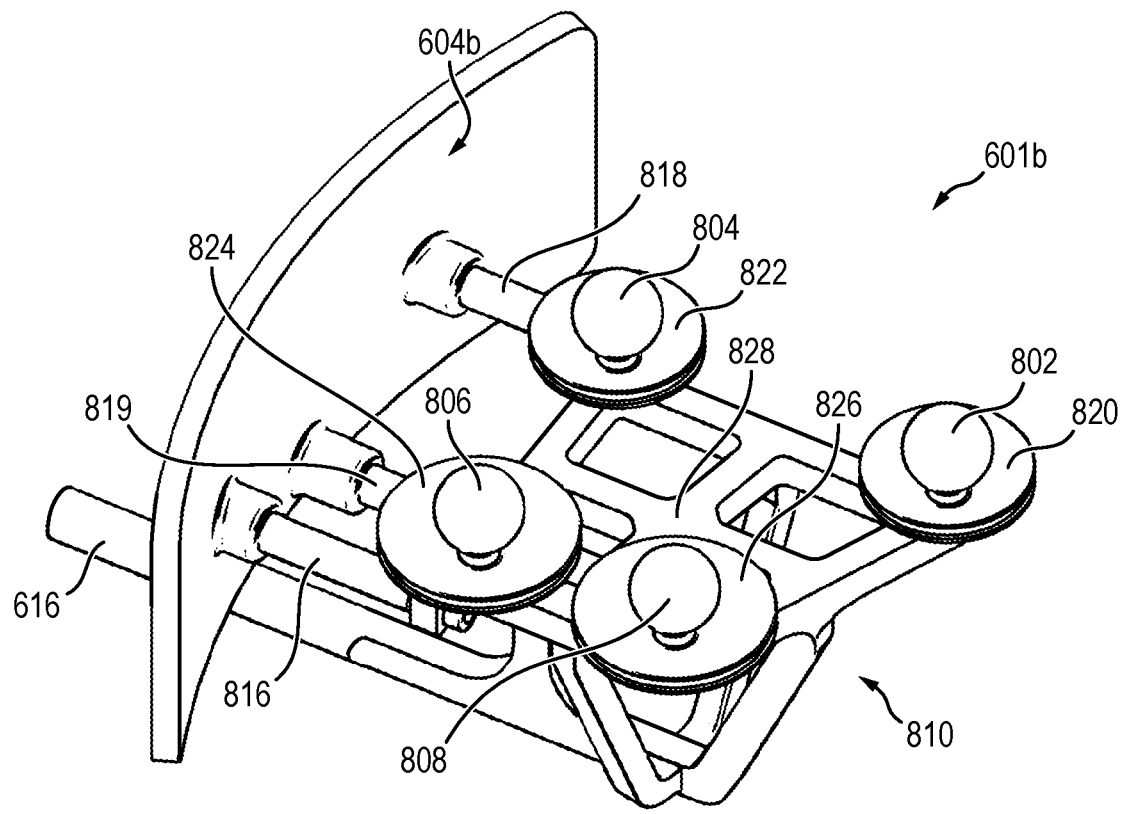
FIG. 8B is an alternative perspective view of the second surgical navigation tracker of FIG. 8A.

FIGS. 7A and 7B illustrate the tracker 601a in greater detail and FIGS. 8A and 8B illustrate the tracker 601b in greater detail. While the trackers 601a and 601b are coupled to different anatomic structures and can include unique geometric arrangements of tracking elements so as to be distinguished from one another, much of the description regarding features of one tracker is applicable to the other. As shown in FIGS. 7A and 7B, the tracker 601a can include a plurality of tracking elements 702, 704, 706, 708 arranged in a fixed geometry relative to one another. Further, the fixed geometry can be unique with respect to any other tracker utilized in a surgical system so that a sensor and associated tracking unit or system can identify which tracker it is viewing by the unique geometric arrangement detected. Further, the fixed geometric arrangement can be utilized by the tracking unit or system to determine a three-dimensional position and orientation of the tracker 601a based on the relation of the various tracking elements 702, 704, 706, 708 in the field of view of the tracking unit sensor(s). Again, this example is provided with regard to an optical tracking system, but in other embodiments alternative types of tracking elements can be employed if a different type of tracking system is utilized. Returning to the illustrated embodiment of a passive optical tracking system, each of the tracking elements 702, 704, 706, 708 can be a reflective optical marker, e.g., a reflective sphere or spherical element configured to reflect at least a certain type of light (e.g., infra-red light, etc.) that can be detected by a sensor, e.g., stereoscopic sensor 220 described above.

The tracking elements 702, 704, 706, 708 can be coupled to a frame 710 that can create a rigid structure and maintain the fixed geometry of the tracking elements relative to the frame and the other tracking elements. The frame can also serve to couple the guard 604a to the arrangement or constellation of tracking elements 702, 704, 706, 708. Further, the frame can include a post 712 extending therefrom, e.g., by being coupled thereto or formed integrally therewith. The post 712 can, for example, extend distally from a proximal portion of the frame 710 having the tracking elements 702, 704, 706, 708 coupled thereto. The post 712 can, in some embodiments, extend distally beyond a position of the guard 604a and can be utilized to couple the tracker 601a to the surgical pins 618, 620 via the attachment mechanism 622. The frame 710 can also include one or more markings 728 or other indicia to aid a user in positioning or registering the tracker 601a. For example, in the illustrated embodiment the marking 728 is an "F" to indicate the tracker 601a should be attached to the patient's femur 606.

The guard 604a can have a variety of shapes and sizes. In some embodiments, the guard 604a can be curved along one or more dimensions thereof. For example, in the illustrated embodiment the guard 604a is curved along a major dimension thereof so as to at least partially surround the tracking elements 702, 704, 706, 708 and more effectively shield them from foreign liquids or matter that might come from a plurality of directions. In other embodiments, the guard 604a can be planar. The guard can also be positioned at a variety of angles relative to the tracking elements to provide greater protection.

The guard 604a can have a variety of shapes, e.g., in the illustrated embodiment the guard 604a is substantially rectangular in shape. In other embodiments, the guard 604a can be elliptical, square, triangular, etc. The guard 604a also includes an angled portion or lip 714 to, e.g., direct liquid or matter from running off the guard in a manner that would result in accumulation on any of the tracking elements 702, 704, 706, 708.

The guard 604a can be coupled to the frame 710 by one or more struts 716, 718, 719 using conventional hardware, such as screws, etc. This can facilitate the interchange of guards having different shapes, sizes, etc. for use in different procedures where different protection of the tracking elements 702, 704, 706, 708 may be needed. Such construction might also facilitate cleaning and sterilization of the guard. In other embodiments, however, the guard 604a can be integrally formed with the frame 710.

Also shown in FIGS. 6A-8B is the inclusion of a second guard 720, 722, 724, 726 disposed adjacent to each tracking element 702, 704, 706, 708. The second guards 720, 722, 724, 726 can be coupled to the tracking elements 702, 704, 706, 708 and, for example, disposed between each tracking element and the frame 710. The second guards 720, 722, 724, 726 can also function to shield a tracking element from foreign matter or liquid. In some embodiments and as shown in the figures, the second guards 720, 722, 724, 726 can be arranged so as to shield the tracking elements 702, 704, 706, 708 from a different angle of attack than the guard 604a. Referring back to FIGS. 6A and 6B, for example, the guard 604a largely shields the tracking elements of the tracker 601a from foreign matter or liquid ejected from the surgical site (e.g., the knee joint in the illustrated embodiment) along a longitudinal axis of the femur 606. The second guards 720, 722, 724, 726 of the tracker 601a are arranged to shield the tracking elements of the tracker 601a along an axis that is perpendicular or otherwise transverse to the longitudinal axis of the femur 606.

As with the guard 604a, the second guards 720, 722, 724, 726 can have a variety of shapes and sizes. The second guards 720, 722, 724, 726 can be smaller than the guard 604a because they each shield individual tracking elements, rather than the entire constellation thereof as in the case of the guard 604a, but can similarly be curved in some embodiments or planar in others. The second guards are configured so as not to hinder the detection of the tracking elements by the tracking unit sensor(s). A curved shape of the guard 604a or the second guards 720, 722, 724, 726 can allow the guards to shield from a plurality of directions simultaneously. Further, the guards can be round as illustrated or have other shapes, such as rectangles, squares, ovals or ellipses, triangles, etc. Besides, second guards may be coupled to only some of the tracking elements, e.g. depending on their risk of exposure to liquids or foreign matter.

Turning to FIGS. 8A and 8B that illustrate the tracker 601b in greater detail, the tracker 601b can include a plurality of tracking elements 802, 804, 806, 808 arranged in a fixed geometry relative to one another. Further, the fixed geometry can be unique with respect to any other tracker utilized in a surgical system so that a sensor and associated tracking unit or system can identify which tracker it is viewing by the unique geometric arrangement detected. Further, the fixed geometric arrangement can be utilized by the tracking unit or system to determine a three-dimensional position and orientation of the tracker 601b based on the relation of the various tracking elements 802, 804, 806, 808 in the field of view of the tracking unit sensor(s). Again, this example is provided with regard to an optical tracking system, but in other embodiments alternative types of tracking elements can be employed if a different type of tracking system is utilized. Returning to the illustrated embodiment of a passive optical tracking system, each of the tracking elements 802, 804, 806, 808 can be a reflective optical marker, e.g., a reflective sphere or spherical element configured to reflect at least a certain type of light (e.g., infra-red light, etc.) that can be detected by a sensor, e.g., stereoscopic sensor 220 described above.

The tracking elements 802, 804, 806, 808 can be coupled to a frame 810 that can create a rigid structure and maintain the fixed geometry of the tracking elements relative to the frame and the other tracking elements. The frame can also serve to couple the guard 604b to the arrangement or constellation of tracking elements 802, 804, 806, 808. Further, the frame can include a post 616 extending therefrom, e.g., by being coupled thereto or formed integrally therewith. The post 616 can, for example, extend distally from a proximal portion of the frame 810 having the tracking elements 802, 804, 806, 808 coupled thereto. The post 616 can, in some embodiments, extend distally beyond a position of the guard 604b and can be utilized to couple the tracker 601b to the surgical pins 610, 612 via the attachment mechanism 614. The frame 810 can also include one or more markings 828 or other indicia to aid a user in positioning or registering the tracker 601 b. For example, in the illustrated embodiment the marking 828 is a "T" to indicate the tracker 601b should be attached to the patient's tibia 608.

The guard 604b can have a variety of shapes and sizes. In some embodiments, the guard 604b can be curved along one or more dimensions thereof. For example, in the illustrated embodiment the guard 604b is curved along a major dimension thereof so as to at least partially surround the tracking elements 802, 804, 806, 808 and more effectively shield them from foreign liquids or matter that might come from a plurality of directions. In other embodiments, the guard 604a can be planar. The guard can also be positioned at a variety of angles relative to the tracking elements to provide greater protection.

The guard 604b can have a variety of shapes, e.g., in the illustrated embodiment the guard 604b is substantially rectangular in shape. In other embodiments, the guard 604b can be elliptical, square, triangular, etc. Note that in the illustrated embodiment the guard 604b does not include the angled portion or lip 714 of the guard 604a, though such a feature could be included in other embodiments.

The guard 604b can be coupled to the frame 810 by one or more struts 816, 818, 819 using conventional hardware, such as screws, etc. This can facilitate the interchange of guards having different shapes, sizes, etc. for use in different procedures where different protection of the tracking elements 802, 804, 806, 808 may be needed. Such construction might also facilitate cleaning and sterilization of the guard. In other embodiments, however, the guard 604b can be integrally formed with the frame 810.

Also shown are second guards 820, 822, 824, 826 disposed adjacent to each tracking element 802, 804, 806, 808. The second guards 820, 822, 824, 826 can be coupled to the tracking elements 802, 804, 806, 808 and, for example, disposed between each tracking element and the frame 810. The second guards 820, 822, 824, 826 can also each function to shield a tracking element from foreign matter or liquid. In some embodiments and as shown in the figures, the second guards 820, 822, 824, 826 can be arranged so as to shield the tracking elements 802, 804, 806, 808 from a different angle of attack than the guard 604b. Referring back to FIGS. 6A and 6B, for example, the guard 604b largely shields the tracking elements of the tracker 601b from foreign matter or liquid ejected from the surgical site (e.g., the knee joint in the illustrated embodiment) along a longitudinal axis of the tibia 608. The second guards 820, 822, 824, 826 of the tracker 601b are arranged to shield the tracking elements of the tracker 601b along an axis that is perpendicular or otherwise transverse to the longitudinal axis of the tibia 608.

As with the guard 604b, the second guards 820, 822, 824, 826 can have a variety of shapes and sizes. The second guards 820, 822, 824, 826 can be smaller than the guard 604b because they each shield individual tracking elements, rather than the entire constellation thereof as in the case of the guard 604b, but can similarly be curved in some embodiments or planar in others. The second guards are configured so as not to hinder the detection of the tracking elements by the tracking unit sensor(s). A curved shape of the guard 604b or the second guards 820, 822, 824, 826 can allow the guards to shield from a plurality of directions simultaneously. Further, the guards can be round as illustrated or have other shapes, such as rectangles, squares, ovals or ellipses, triangles, etc. Besides, second guards may be coupled to only some of the tracking elements, e.g. depending on their risk of exposure to liquids or foreign matter.

As noted above, any of a variety of surgical procedures can be performed utilizing the surgical navigation trackers described herein. For example, one procedure that can benefit from the present disclosure is a robot-assisted total knee arthroplasty. Other exemplary procedures can include any procedure throughout the body requiring an osteotomy step, including various orthopedic procedures throughout the body, including various spinal surgeries, etc.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The instruments, devices, and systems disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can have varying degrees of rigidity or flexibility, as appropriate for their use. Device sizes can also vary greatly, depending on the intended use and surgical site anatomy. Furthermore, particular components can be formed from a different material than other components. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices, systems, and methods disclosed herein can be used in minimally-invasive surgery and/or open surgery. While the devices and methods disclosed herein are generally described in the context of orthopedic surgery on a human patient, it will be appreciated that the methods and devices disclosed herein can be used in any of a variety of surgical procedures with any human or animal subject, or in non-surgical procedures.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

We disclose a surgical system, comprising:
 a surgical device having an end effector configured to manipulate tissue; and
 a surgical navigation tracker configured to be coupled to any of a surgical instrument and an anatomical structure, the surgical navigation tracker including a tracking element and a guard configured to be positioned between the tracking element and the end effector; and
 a tracking unit configured to determine a position of the surgical navigation tracker.

The system of paragraph 0088, wherein the surgical navigation tracker includes a plurality of tracking elements arranged in a fixed geometry relative to one another.

The system of paragraph 0089, wherein the plurality of tracking elements are reflective optical markers.

The system of paragraph 0089, further comprising a plurality of second guards, wherein each second guard is disposed adjacent to one of the plurality of tracking elements.

The system of paragraph 0091, wherein each second guard is configured to shield its adjacent tracking element from a first direction.

The system of paragraph 0091, wherein each second guard is configured to shield its adjacent tracking element from a plurality of directions.

The system of paragraph 0092, wherein the guard of the surgical navigation tracker is configured to shield the plurality of tracking elements from a second direction that is different from the first direction.

The system of paragraph 0089, wherein the guard of the surgical navigation tracker is configured to shield the plurality of tracking elements.

The system of paragraph 0095, wherein the guard of the surgical navigation tracker is configured to shield the plurality of tracking elements from a plurality of directions.

The system of paragraph 0088, wherein the guard of the surgical navigation tracker is curved.

The system of paragraph 0088, wherein the surgical navigation tracker includes a pin for coupling the tracker to the anatomical structure and the guard is disposed between the pin and the tracking element.

The system of paragraph 0088, wherein the surgical navigation tracker includes a frame to which the tracking element and the guard are coupled.

A surgical navigation tracker, comprising:
 a frame having a post extending distally therefrom;
 a tracking element coupled to the frame along a proximal portion thereof; and
 a guard coupled to the frame such that the guard is disposed distally of the tracking element and the post extends distally beyond the guard.

The tracker of paragraph 0100, wherein the tracking element comprises a plurality of tracking elements that are each coupled to the frame in a fixed geometry relative to one another.

The tracker of paragraph 0091, wherein the tracking element is a reflective optical marker.

The tracker of paragraph 0091, further comprising a second guard coupled to the tracking element.

The tracker of paragraph 0103, wherein the second guard is disposed between the tracking element and the frame.

The tracker of paragraph 0103, wherein the second guard is configured to shield the tracking element from a first direction and the guard is configured to shield the tracking element from a second direction that is different from the first direction.

The tracker of paragraph 0103,
 wherein the tracking element comprises a plurality of tracking elements and the second guard comprises a plurality of second guards each disposed adjacent to one of the plurality of tracking elements; and
 wherein each second guard is configured to shield its adjacent tracking element and the guard is configured to shield the plurality of tracking elements.

The tracker of paragraph 0104, wherein the second guard is configured to shield the tracking element from a plurality of directions.

The tracker of paragraph 0091, wherein a distal end of the post is coupled to a surgical pin.

The tracker of paragraph 0091, wherein the guard is configured to shield a tracking element from a plurality of directions.

A surgical method, comprising:
 positioning a surgical robot relative to a patient's knee such that a cutting tool coupled to the robot can make one or more cuts to any of a distal end portion of the patient's femur and a proximal end portion of the patient's tibia;
 coupling a first surgical navigation tracker to the patient's femur such that a guard of the first surgical navigation tracker is disposed between the cutting tool and one or more tracking elements of the first surgical navigation tracker; and
 coupling a second surgical navigation tracker to the patient's tibia such that a guard of the second surgical navigation tracker is disposed between the cutting tool and one or more tracking elements of the first surgical navigation tracker.

One skilled in the art will appreciate further features and advantages based on the above-described embodiments. Accordingly, the disclosure is not to be limited by what has been particularly shown and described. All publications and references cited herein are expressly incorporated herein by reference in their entirety.

The invention claimed is:

1. A surgical navigation tracker, comprising:
a frame;
a plurality of tracking elements coupled to the frame and arranged in a fixed geometry relative to one another; and
a guard coupled to the frame and spaced apart from the plurality of tracking elements to shield at least two of the plurality of tracking elements from liquid or foreign matter from at least one direction, wherein the guard does not cover any of the plurality of tracking elements.

2. The tracker of claim 1, wherein the plurality of tracking elements are reflective optical markers.

3. The tracker of claim 1, wherein the guard is a first guard, further comprising a plurality of second guards interposed between the frame and the plurality of tracking elements, each tracking element having an adjacent second guard.

4. The tracker of claim 3, wherein the first guard is larger than each of the second guards.

5. The tracker of claim 4, wherein at least one of the first guard or each of the second guards is curved.

6. The tracker of claim 4, wherein the first guard is generally rectangular and each of the second guards is round.

7. The tracker of claim 1, wherein each second guard is configured to shield its adjacent tracking element from a direction, wherein the direction shielded by the second guards is not the same as the direction is shielded by the first guard, and wherein the second guards do not cover any of the plurality of tracking elements.

8. The tracker of claim 1, wherein the guard is curved.

9. The tracker of claim 8, wherein the guard is configured to shield a tracking element from a plurality of directions.

10. The tracker of claim 1, further comprising a pin for coupling the tracker to an anatomical structure, the guard being disposed between the pin and the plurality of tracking elements.

11. The tracker of claim 10, further comprising a post extending distally from the frame to couple the tracker to the pin.

12. A surgical system, comprising:
a surgical device having an end effector configured to manipulate tissue;
the surgical navigation tracker of claim 1; and
a tracking unit configured to determine a position of the surgical navigation tracker.

13. The tracker of claim 1, wherein the guard further comprises a lip to direct a flow of the liquid or foreign matter.

14. A surgical navigation tracker, comprising:
a frame;
a plurality of tracking elements coupled to the frame and arranged in a fixed geometry relative to one another;
a first guard coupled to the frame and spaced apart from the plurality of tracking elements;
a plurality of second guards interposed between the frame and the plurality of tracking elements, each tracking element having an adjacent second guard;
wherein neither the first guard nor any of the plurality of second guards covers any of the plurality of tracking elements.

15. The tracker of claim 14, wherein the first guard shields at least two of the plurality of tracking elements from liquid or foreign matter from a first direction, wherein each second guard is configured to shield its adjacent tracking element from liquid or foreign matter from a second direction, and wherein the first direction and the second direction are different.

16. The tracker of claim 15, wherein the first guard further comprises a lip to direct a flow of the liquid or foreign matter.

17. The tracker of claim 16, wherein the first guard is curved.

18. The tracker of claim 15, wherein the second direction is from a frame side of the tracker.

19. The tracker of claim 15, further comprising a post extending distally from the frame, a distal end of the post having a pin for coupling the tracker to an anatomical structure, the first guard being disposed between the pin and the plurality of tracking elements.

20. The tracker of claim 19, wherein the first direction is from a pin side of the tracker.

21. A surgical system, comprising:
a surgical device having an end effector configured to manipulate tissue;
a pair of surgical navigation trackers of claim 19, and
a tracking unit configured to determine a position of each of the surgical navigation trackers;
wherein the end effector contacts the anatomical structure between the pair of surgical navigation trackers.

22. The surgical system of claim 21, wherein each first guard shields at least two of its corresponding plurality of tracking elements from liquid or foreign matter from a first direction relative to the end effector, and wherein each second guard is configured to shield its adjacent tracking element from liquid or foreign matter from a second direction that is other than the first direction.

* * * * *